United States Patent
Brisben et al.

(10) Patent No.: US 11,089,958 B2
(45) Date of Patent: Aug. 17, 2021

(54) SYSTEMS AND METHODS FOR MANAGING PATIENT-TRIGGERED EPISODES

(71) Applicant: Cardiac Pacemakers, Inc., St. Paul, MN (US)

(72) Inventors: Amy Jean Brisben, Saint Paul, MN (US); Qi An, Blaine, MN (US); Pramodsingh Hirasingh Thakur, Woodbury, MN (US); David J. Ternes, Roseville, MN (US); JoAnna Trapp Simpson, Eagan, MN (US); Viktoria A. Averina, Shoreview, MN (US); Deepa Mahajan, North Oaks, MN (US); Sunipa Saha, Shoreview, MN (US); Krzysztof Z. Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 415 days.

(21) Appl. No.: 16/027,670

(22) Filed: Jul. 5, 2018

(65) Prior Publication Data

US 2019/0008384 A1 Jan. 10, 2019

Related U.S. Application Data

(60) Provisional application No. 62/528,834, filed on Jul. 5, 2017.

(51) Int. Cl.
*A61N 1/365* (2006.01)
*A61B 5/00* (2006.01)
(Continued)

(52) U.S. Cl.
CPC .......... *A61B 5/0006* (2013.01); *A61B 5/0022* (2013.01); *A61B 5/332* (2021.01);
(Continued)

(58) Field of Classification Search
CPC ....... A61B 5/0031; A61B 5/335; A61B 5/349; A61B 5/7232; A61N 1/3702; A61N 1/3706
See application file for complete search history.

(56) References Cited

U.S. PATENT DOCUMENTS

| | | | |
|---|---|---|---|
| 2010/0234914 A1* | 9/2010 | Shen | A61N 1/3706 607/17 |
| 2018/0064350 A1 | 3/2018 | Thakur et al. | |
| 2019/0008384 A1* | 1/2019 | Brisben | A61B 5/0022 |

OTHER PUBLICATIONS

"2012 ACCF/AHA/HRS Focused Update Incorporated Into the ACCF/AHA/HRS 2008 Guidelines for Device-Based Therapy of Cardiac Rhythm Abnormalities", Journal of the American College of Cardiology, vol. 61, No. 3, (2013), e6-e75.

(Continued)

*Primary Examiner* — Jon Eric C Morales
(74) *Attorney, Agent, or Firm* — Schwegman Lundberg & Woessner, P.A.

(57) ABSTRACT

Systems and methods for managing machine-generated medical events detected from one or more patients are described herein. A medical event management system includes an event analyzer circuit to detect a medical event using physiological data from a patient-triggered episode acquired from a medical device. The event analyzer circuit determines a confidence score of the medical event detection, and generates an alignment indicator indicating a degree of concordance between the detected medical event and the information about the patient-triggered episode. The system assigns priority information to the patient-triggered episode using the generated alignment indicator and the confidence score of the detection. An output circuit can output the received physiological information to a user or a process according to the assigned priority information.

20 Claims, 7 Drawing Sheets

(51) Int. Cl.
        *A61B 5/332*        (2021.01)
        *A61B 5/363*        (2021.01)
        *A61B 5/364*        (2021.01)
        *A61B 5/0464*       (2006.01)
(52) U.S. Cl.
        CPC ............. *A61B 5/363* (2021.01); *A61B 5/364* (2021.01); *A61B 5/686* (2013.01); *A61B 5/7221* (2013.01)

(56) References Cited

OTHER PUBLICATIONS

"Guidelines for the diagnosis and management of syncope", EHJ 30, (2009), 2631-2671.
Balmelli, Nicola, et al., "Diagnostic Yield of Automatic and Patient-Triggered Ambulatory Cardiac Event Recording in the Evaluation of Patients with Palpitations, Dizziness, or Syncope", Clin. Cardiol. 26, 173-176 (2003).
Sun, B., et al., "Direct Medical Costs of Syncope-Related Hospitalizations in the United States", The American Journal of Cardiology vol. 95, (Mar. 1, 2005), 668-671.

* cited by examiner

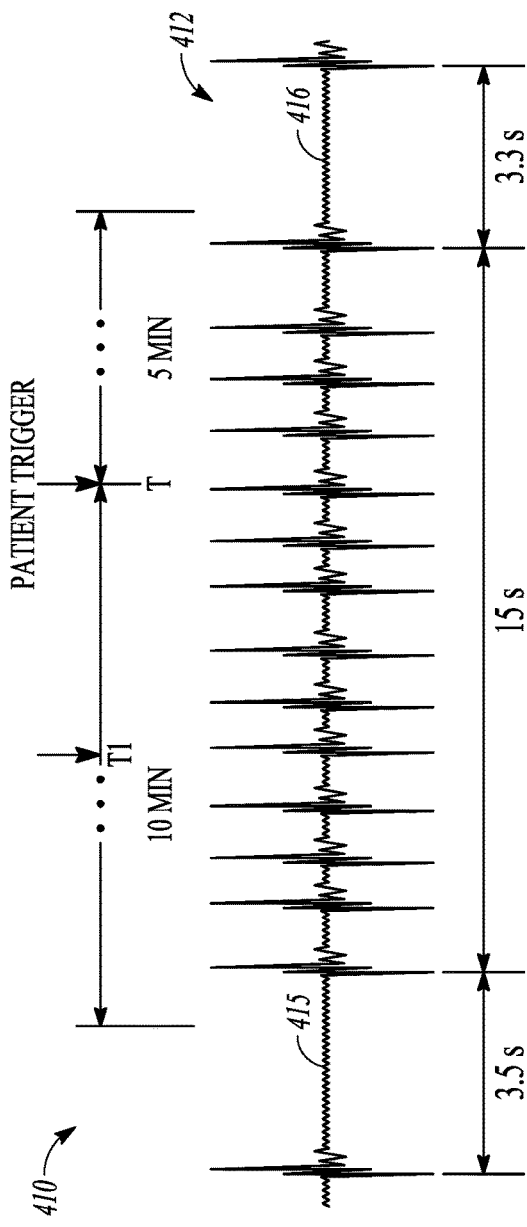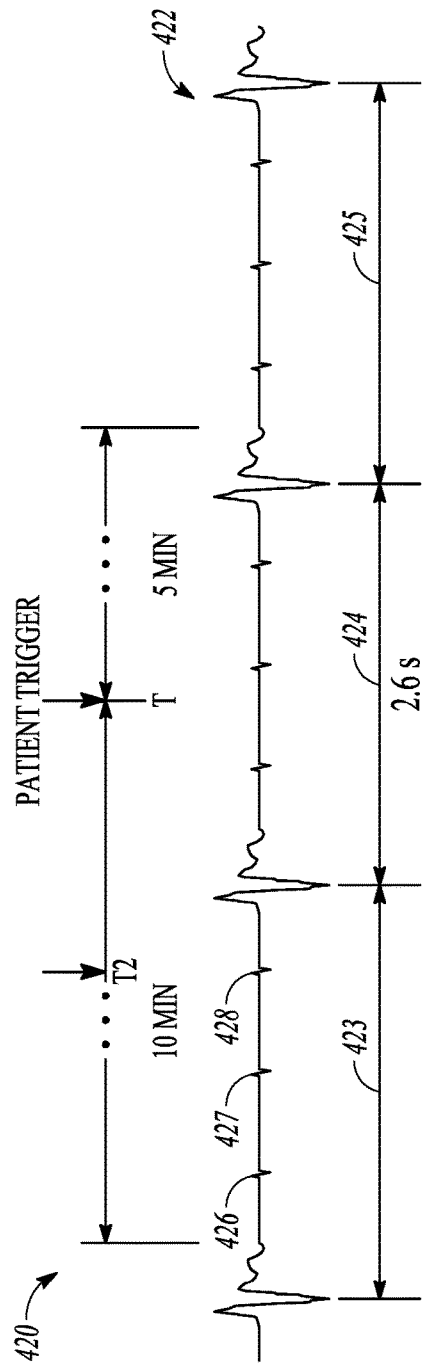
FIG. 4A
FIG. 4B

SYSTEMS AND METHODS FOR MANAGING PATIENT-TRIGGERED EPISODES

CLAIM OF PRIORITY

This application claims the benefit of priority under 35 U.S.C. § 119(e) of U.S. Provisional Patent Application Ser. No. 62/528,834, filed on Jul. 5, 2017, which is herein incorporated by reference in its entirety.

TECHNICAL FIELD

This document relates generally to automated patient management, and more particularly, to systems, devices and methods for managing event episodes detected by a medical device.

BACKGROUND

Implantable medical devices (IMDs) have been used for monitoring patient health condition or disease states and delivering therapies. For example, implantable cardioverter-defibrillators (ICDs) are used to monitor certain abnormal heart rhythms. Some IMDs may be used to monitor progression of a chronic disease, such as worsening of cardiac performance due to congestive heart failure (CHF). In addition to diagnostic capabilities, the IMDs may also provide therapies to treat or alleviate certain medical conditions, such as cardiac electrostimulation therapies to treat cardiac arrhythmias or to rectify cardiac dyssynchrony in CHF patients.

The IMDs may generate patient alert notification upon a detection of a particular health condition or a medical event, such as a cardiac arrhythmia or worsening heart failure (WHF). Some IMDs may register a patient-triggered episode of a medical event, and record physiological data in response to the patient trigger. The alert notification may be provided to a healthcare provider to signal the patient health condition. Upon being notified, the healthcare provider may review the recorded physiological data associated with the episode of medical event, determine the presence of or possible causes leading to the medical event, or assess whether a prescribed therapy has resulted in desired therapeutic outcome.

A patient management system may monitor patients with IMDs that are interconnected to the patient management via a data communication network. Such a patient management system may allow a healthcare provider to follow up with the patients remotely, or to assess device functions on a periodic basis.

OVERVIEW

A patient management system may manage a large volume of alert notifications corresponding to medical events reported by ambulatory medical devices (AMDs). For example, in managing a cohort of AMD patients in a clinic, the patient management system may frequently receive alert notifications on various cardiac arrhythmia episodes or worsening heart failure (WHF) events detected by the implantable cardiac devices, such as a cardiac monitor, a pacemaker, an implantable defibrillator, or a cardiac resynchronization therapy device. In addition to the device-detected medical events, some AMDs may also register patient-triggered episodes such as when the patient demonstrates certain signs or symptoms, or experiences a precursor event indicative of a medical event (e.g., cardiac arrhythmias, syncope, or WHF events). Patient-triggered episodes can be cost effective, and have been shown to increase diagnostic yield in some patients. Physiological data associated with the device-detected medical events or patient-triggered episodes may be transmitted to a patient management system, where a clinician may review the detections and the physiological data, take further actions such as adjudicate the event detections, schedule patient follow-up visits, or reprogram the AMDs. The clinician may also associate patient symptoms with physiological substrates based on the physiological data. Such an association may be used to guide clinical decisions such as AMD implantation or adjustment of therapy.

With a large number of AMDs connected to the patient management system, reviewing medical events from all the patients requires significant amount of time and resources, and can be costly or otherwise time consuming for a healthcare facility. Although patient-triggered episodes may provide additional diagnostic benefits in some patients, such episodes may not be sufficiently reliable predictors of a target medical event in some other patients. Patient-triggered episodes may not always correspond to the automatic device-based medical event detections. The present inventors have recognized a substantial challenge in efficient medical alert management, and particularly a need for an approach to evaluate, prioritize, and present alert notifications of the device-reported events or patient-triggered episodes. Such systems and methods may help align medical resources to serve those patients with critical medical conditions.

This document discusses, among other things, systems, devices, and methods for evaluating and prioritizing medical events generated by a medical device such as an AMD. A data management system may include an event analyzer circuit to detect a medical event using physiological information corresponding to a patient-triggered episode, and determine a confidence score associated with that detection. The event analyzer circuit may generate an alignment indicator indicating a degree of concordance between the patient-triggered episode and the medical event detection. An event prioritizer circuit may assign priority information to the patient-triggered episode using the alignment indicator and the confidence score. An output circuit may output the episode to a user or a process according to the assigned priority information.

Example 1 is a system for prioritizing medical events detected by an ambulatory medical device (AMD). The system comprises: a receiver circuit configured to receive physiological information from the AMD corresponding to a patient-triggered episode; an event analyzer circuit configured to analyze the received physiological information corresponding to the patient-triggered episode, and to determine a confidence score for the patient-triggered episode; and an event prioritizer circuit configured to assign priority information to the received patient-triggered episode using the confidence score.

In Example 2, the subject matter of Example 1 optionally includes the event analyzer circuit that may perform offline analysis of the received physiological information corresponding to the patient-triggered episode.

In Example 3, the subject matter of Example 1 optionally includes the patient-triggered episode that may include information about patient-reported sign or symptom. The event analyzer circuit may detect a medical event and generate an alignment indicator indicating a concordance between the information about patient-reported sign or symptom and the detected medical event.

In Example 4, the subject matter of Example 3 optionally includes the event analyzer circuit that may determine the confidence score using a signal to noise ratio (SNR) of physiological data from the received physiological information.

In Example 5, the subject matter of any one or more of Examples 3-4 optionally includes the event analyzer circuit that may determine the confidence score using information about temporal relationship between the information about patient-reported sign or symptom and the detected medical event.

In Example 6, the subject matter of any one or more of Examples 3-5 optionally includes the event prioritizer circuit that may assign the priority information to the patient-triggered episode including one or more of: a high priority if the confidence score exceeds a score threshold and the alignment indicator indicates a concordance between the patient-triggered episode and the detected medical event; a low priority if the confidence score exceeds a score threshold and the alignment indicator indicates a discordance between the patient-triggered episode and the detected medical event; or a medium priority if the confidence score falls below the score threshold.

In Example 7, the subject matter of any one or more of Examples 3-6 optionally includes the event analyzer circuit that may detect the medical event further using patient medical history data.

In Example 8, the subject matter of any one or more of Examples 1-7 optionally includes the event prioritizer circuit that may assign the priority information further using a similarity metric between the patient-triggered episode and one or more patient historical episodes.

In Example 9, the subject matter of any one or more of Examples 1-8 optionally includes the event analyzer circuit that may consolidate two or more patient-triggered episodes into a cluster, and determine a representative episode for the cluster. The event prioritizer circuit may assign the priority information to the representative episode.

In Example 10, the subject matter of any one or more of Examples 1-9 optionally comprises an external device operatively in communication with the AMD. The external device may include one or more of the receiver circuit, the event analyzer circuit, or the event prioritizer circuit.

In Example 11, the subject matter of Example 10 optionally includes the external device that may receive from the AMD the physiological information corresponding to the patient-triggered episode when the AMD fails to detect a medical event, and detect the medical event via the event analyzer circuit with a higher sensitivity than the AMD in detecting the medical event.

In Example 12, the subject matter of any one or more of Examples 1-11 optionally includes the physiological information that may include cardiac electrical activity data corresponding to a patient-triggered syncopal episode. The event analyzer circuit may detect a cardiac arrhythmia using the cardiac electrical activity data, determine a confidence score about the detected cardiac arrhythmia being predictive of syncope, and generate an alignment indicator indicating a degree of concordance between the patient-triggered episode and the detected cardiac arrhythmia.

In Example 13, the subject matter of Example 12 optionally includes the cardiac arrhythmia that may include a cardiac pause, and the event analyzer circuit may determine the confidence score about the detected pause being predictive of syncope using one or more of: a signal to noise ratio (SNR) of the cardiac electrical activity data, or a detection of far field cardiac electrical activity during the cardiac pause.

In Example 14, the subject matter of any one or more of Examples 1-13 optionally comprises an output circuit that may rank a plurality of patient-triggered episodes in a specific order of the assigned priority information, and present one or more of the ranked plurality of patient-triggered episodes to a user or a process.

In Example 15, the subject matter of Example 14 optionally includes the output circuit that may generate a recommendation for adjusting AMD programming using the confidence score.

Example 16 is a system for prioritizing medical events detected by an ambulatory medical device (AMD). The system comprises: a receiver circuit configured to receive physiological data from the AMD and information about patient-reported sign or symptom; an event analyzer circuit configured to analyze the received physiological data to detect a medical event, and to generate an alignment indicator indicating a concordance between the information about patient-reported sign or symptom and the detected medical event; and an event prioritizer circuit configured to assign priority information to the detected medical event using the alignment indicator.

Example 17 is a method for prioritizing medical events detected by an ambulatory medical device (AMD). The method comprising steps of: receiving, via a receiver circuit, physiological information corresponding to a patient-triggered episode; analyzing the received physiological information corresponding to the patient-triggered episode via an event analyzer circuit to detect a medical event; determining a confidence score for the patient-triggered episode; assigning priority information to the received physiological information via an event prioritizer circuit using the confidence score.

In Example 18, the subject matter of Example 17 optionally includes generating an alignment indicator. The patient-triggered episode may include information about patient-reported sign or symptom, and the alignment indicator indicates a concordance between the information about patient-reported sign or symptom and the detected medical event.

In Example 19, the subject matter of Example 18 optionally includes determining the confidence score of medical event detection includes using one or more of: a signal to noise ratio (SNR) of physiological data in the received physiological information, or information about temporal alignment between the information about patient-reported sign or symptom and the detected medical event.

In Example 20, the subject matter of Example 18 optionally includes assigning the priority information to the patient-triggered episode including assigning one or more of: a high priority if the confidence score exceeds a score threshold and the alignment indicator indicates a concordance between the patient-triggered episode and the detected medical event; a low priority if the confidence score exceeds a score threshold and the alignment indicator indicates a discordance between the patient-triggered episode and the detected medical event; or a medium priority if the confidence score falls below the score threshold.

In Example 21, the subject matter of Example 17 optionally includes receiving the physiological information corresponding to the patient-triggered episode when the AMD fails to detect the medical event, and detecting the medical event using the event analyzer circuit with a higher sensitivity than the AMD.

In Example 22, the subject matter of Example 17 optionally includes the physiological information that may include cardiac electrical activity data corresponding to a patient-triggered syncopal episode. The medical event includes a cardiac pause indicative of syncope. The method in this example comprises steps of: detecting the cardiac pause using the cardiac electrical activity data; determining a confidence score about the detected pause being predictive of syncope using one or more of a signal to noise ratio (SNR) of the cardiac electrical activity data or a detection of far field cardiac electrical activity during the cardiac pause; and generating an alignment indicator indicating a degree of concordance between the patient-triggered episode and the detected cardiac pause.

In Example 23, the subject matter of Example 17 optionally includes ranking a plurality of patient-triggered episodes in a specified order of the assigned priority information, and outputting one or more of the ranked plurality of patient-triggered episodes to a user or a process.

The systems, devices, and methods discussed in this document may improve the technology of automated alert management. One of the challenges in medical alert management is that clinicians need to attend to overwhelmingly large amount of alert notifications. The present document provides a technological solution to this challenge by prioritizing the alert notifications based on the confidence of the detection and an alignment measure between the detection and the patient-triggered episode. For example, a high priority may be assigned to a patient-triggered event if an external device detects the medical event (e.g., cardiac arrhythmia, syncope, or WHF) with a high confidence and the detection concords with the patient-triggered episode in time or in a severity of the medical event. Compared to conventional alert systems, the prioritization of patient-triggered events may improve the alert management system's accuracy of recognizing high-severity medical events (i.e., lower false alert rate) and timely alerting clinicians of such an effect, yet at little to no additional cost or system complexity. Furthermore, an offline analysis of physiological data collected by an AMD near a patient-triggered event may increase the yield of finding the alignment of symptoms and a physiological substrate of an anomaly, such as bradycardia or tachycardia, which is needed documentation to justify evidence-based practice of implanting an AMD to treat conditions such as syncope.

The medical event prioritization discussed in this document may also improve the functionality of a patient management system. The medical event prioritization as discussed herein may be configured to evaluate and prioritize events reported by various medical devices. The event prioritization may be implemented in, and executed by, an AMD or an external system such as a communicator, mobile monitor, programmer, or a remote patient management system in communication with patient AMDs. As such, in some cases, improved alert management may be achieved without a modification of existing patient AMDs or medical event detectors. Because only medical events with higher priority and/or clinically more relevant to medical diagnosis may be stored in the system for clinician review or adjudication, the system memory usage may be more efficient that a traditional data management system.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 4A-B illustrates generally graphs of patient-triggered episodes and priority information assigned to these episodes.

DETAILED DESCRIPTION

Disclosed herein are systems, devices, and methods for managing machine-generated medical alerts associated with medical events detected from one or more patients. A patient management system may include an event analyzer circuit to detect a medical event using physiological information corresponding to a patient-triggered episode. The event analyzer circuit determines a confidence score of the detection, and generates an alignment indicator indicating a degree of concordance between the detected medical event and the episode registered in the AMD. The system may assign priority information to the patient-triggered episode using the generated alignment indicator and the confidence score. An output circuit may output the episode to a user or a process according to the assigned priority information.

Figure 1:
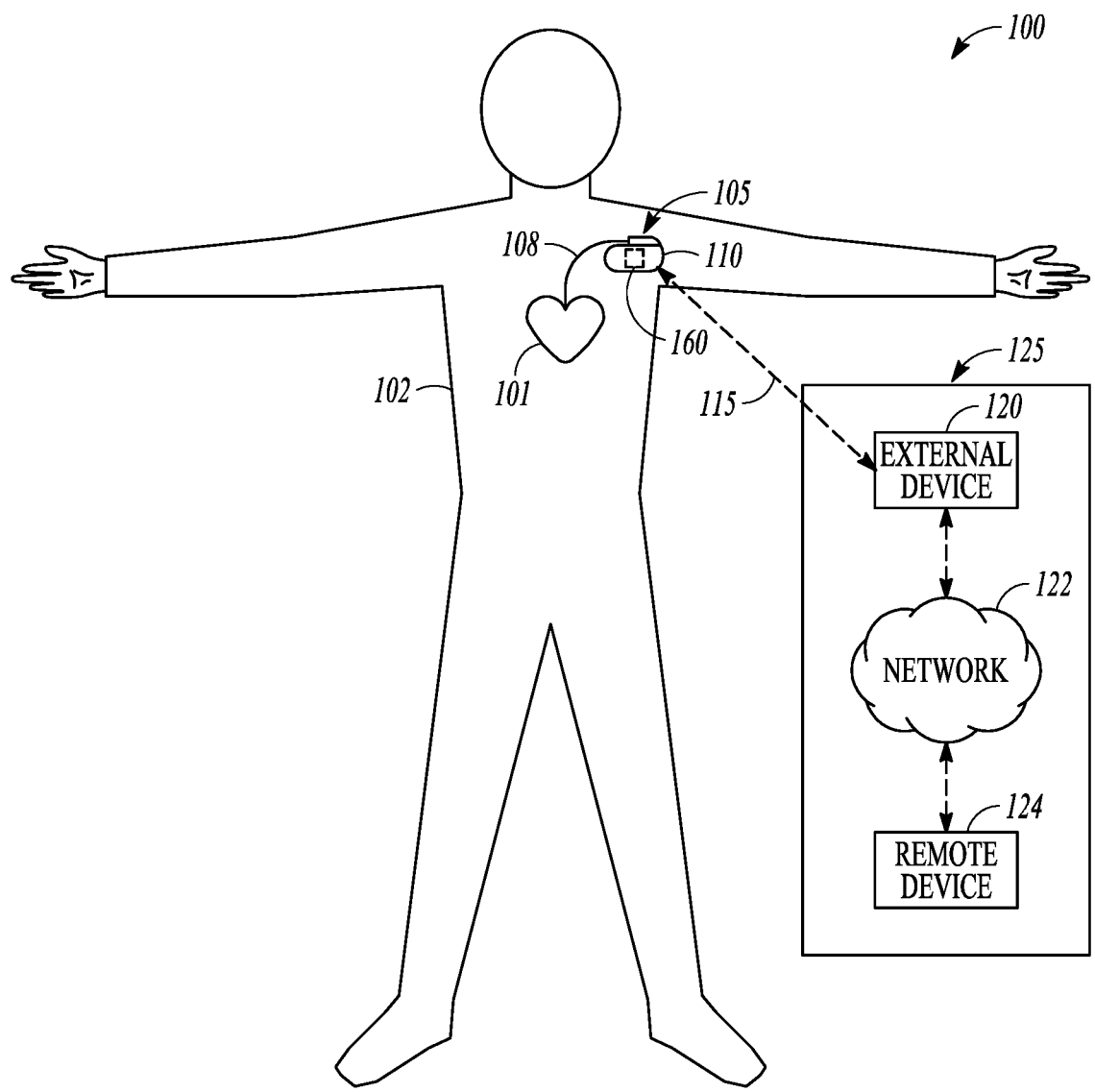
FIG. 1 illustrates generally an example of a patient management system and portions of an environment in which the system may operate.

FIG. 1 illustrates generally an example of a patient management system 100 and portions of an environment in which the system 100 may operate. The patient management system 100 may perform a range of activities, including remote patient monitoring and diagnosis of a disease condition. Such activities can be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiological signal indicative of cardiac activity, or physiological responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiological signal containing information about patient heart rate or pulse rate. In an example, the ambulatory system 105 may include one or more leadless sensors not being tethered to the AMD 110 via the lead system 108. The leadless ambulatory sensors may be configured to sense a physiological signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiological response to activity, posture, respiration rate, tidal volume, respiratory sounds, body weight, or body temperature.

The AMD 110 may include a detector circuit 160 to detect a medical event using the sensed physiological signals. In an example, the medical event includes a specific cardiac arrhythmia, such as atrial fibrillation, atrial flutter, atrial tachycardia, supraventricular tachycardia, ventricular tachycardia, or ventricular fibrillation, among other brady- or tachy-arrhythmias. In an example, the detector circuit 160 is configured to detect syncope, such as one or more of cardiogenic syncope, orthostatic hypotension, or neurally medical syncope such as vasovagal syncope, among others. The detector circuit 160 may detect a presyncopal event or a precipitating event that may lead to a full-blown syncope, such as a cardiac pause or asystole, posture change or posture pattern, physical activities, among others. In some examples, the detector circuit 160 is configured to detect worsening of a chronic medical condition, such as worsening heart failure (WHF).

The detector circuit 160 may execute a detection algorithm to monitor one or more physiological signals continuously or periodically, and to detect the medical event automatically. Additionally or alternatively, the detector circuit 160 may be configured to operate in a patient-triggered mode, register a patient-triggered episode and record physiological data in response to a user-activated trigger. The trigger may be activated by the patient when the patient demonstrates certain signs or symptoms, or experiences a precursor event indicative of a medical event.

The AMD 110 may alternatively be configured as a therapeutic device configured to treat arrhythmia or other heart conditions. The AMD 110 may additionally include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmias, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmias or complications from arrhythmias.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiological data, performing at least one self-diagnostic test (such as for a device operational status), analyzing the physiological data to detect a cardiac arrhythmias, or optionally delivering or adjusting a therapy to the patient 102. Additionally, the external system 125 may receive device data from the AMD 110 via the communication link 115. Examples of the device data received by the external system 125 may include real-time or stored physiological data from the patient 102, diagnostic data such as detection of cardiac arrhythmias or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example. "strong" Bluetooth or IEEE 802.11 wireless fidelity "WiFi"

interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data may be collected by the AMD 110, among other data acquisition sensors or devices associated with the patient 102. The server may include a memory device to store the patient data in a patient database. The server may include an alert analyzer circuit to evaluate the collected patient data, such as associated with patient-triggered episodes, to determine if specific alert condition is satisfied. Satisfaction of the alert condition may trigger a generation of alert notifications. In an example, the alert analyzer circuit may detect the medical event and determine a confidence score of the medical event detection using the received physiological data, generate an alignment indicator indicating a degree of concordance between the received physiological information and the detected medical event, and assign priority information to the patient-triggered episode using the generated alignment indicator and the confidence score. In sonic examples, the alert conditions may be evaluated by the AMD 110. By way of example, alert notifications may include a Web page update, phone or pager call, E-mail, SMS, text or "Instant" message, as well as a message to the patient and a simultaneous direct notification to emergency services and to the clinician. Other alert notifications are possible. The server may include a medical event prioritizer circuit configured to prioritize the alert notifications. For example, an alert of a detected medical event may be prioritized using a similarity metric between the physiological data associated with the detected medical event to physiological data associated with the historical alerts. Examples of the alert analyzer and prioritizer circuits are discussed below, such as with reference to FIGS. 4-5.

The remote device 124 may additionally include one or more locally configured clients or remote clients securely connected over the network 122 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. The remote device 124, including the server and the interconnected clients, may execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a system user such as the patient or a clinician, or to a process including, for example, an instance of a computer program executable in a microprocessor. In an example, the process may include an automated generation of recommendations for a therapy, or a recommendation for further diagnostic test or treatment. In an example, the external device 120 or the remote device 124 may respectively include display units for displaying the physiological or functional signals, or alerts, alarms, emergency calls, or other forms of warnings to signal the detection of arrhythmias. In some examples, the external system 125 may include an external data processor configured to analyze the physiological or functional signals received by the AMD 110, and to confirm or reject the detection of the medical events. Computationally intensive algorithms, such as machine-learning algorithms, may be implemented in the external data processor to process the data retrospectively to detect cardia arrhythmias.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
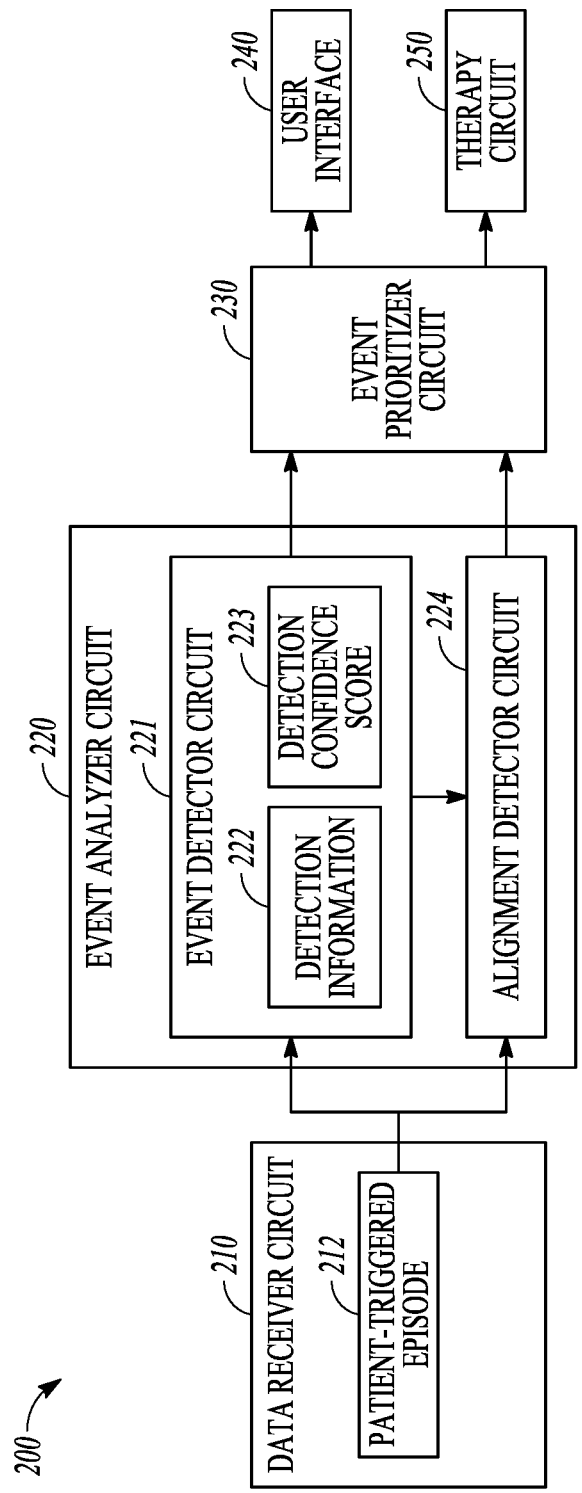
FIG. 2 illustrates generally an example of a medical event management system configured to prioritize medical events such as detected by an ambulatory medical device.

FIG. 2 illustrates generally an example of a medical event management system 200 that may be configured to prioritize medical events detected by a medical device. At least a portion of the alert management system 200 may be implemented in the external system 125 such as one or more of the external device 120 or the remote device 124, or distributed between the AMD 110 and the external system 125. The alert management system 200 may include one or more of a data receiver circuit 210, an event analyzer circuit 220, an event prioritizer circuit 230, and a user interface 240. The alert management system 200 may additionally be configured as a therapeutic system that includes an optional therapy circuit 250 for delivering a therapy to treat a disease or to alleviate a medical condition.

The data receiver circuit 210 may receive physiological information of a target medical event. The episode of the medical event may include a patient-triggered episode 212 registered by the AMD. Additionally or alternatively, the episode of the medical event may include an event detected by an AMD, such as through dedicated circuits or processors executing instructions to monitor one or more physiological signals continuously or periodically, and to detect the medical event automatically. In an example, the data receiver circuit 210 may be communicatively coupled to the AMD 110, and receive the physiological data from the AMD 110 through the communication link 115. The physiological signals sensed from a patient may be stored in a storage device within the AMD, or separated from the AMD 110 such as an electronic medical record (EMR) system. The information about the patient-triggered episode 212 may include patient input about presence or absence of a target medical event, severity of symptoms, timing information of the symptoms, such as onset and termination time of the patient-triggered episode, among others. The patient-triggered episode 212 may additionally include physiological data collected in response to the patient trigger. The physiological data may include physiological signals sensed from one or more physiological sensors. Examples of the patient-triggered episodes are discussed below, such as with reference to FIG. 3.

The event analyzer circuit 220 and the event prioritizer circuit 230 may be implemented as parts of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

One or more of the event analyzer circuit 220 or the event prioritizer circuit 230 may respectively include circuit sets comprising one or more other circuits or sub-circuits. For example, as illustrated in FIG. 2, the event analyzer circuit 220 may include an event detector circuit 221 and an alignment detector circuit 224. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The event detector circuit 221 may be coupled to the data receiver circuit 210, and detect a target medical event using the received episode, such as the physiological data of the patient-triggered episode 212 registered by the AMD 110. The medical event detection may result in detection information 222 and detection confidence score 223. The detection information 222 may include a detection decision of presence or absence of a target medical event, severity of the condition, or timing of an onset or a termination of the detected medical event. The event detector circuit 221 may use a detection algorithm different from the one used by the AMD to detect the target medical event. In an example, the event detector circuit 221 has more computational and processing power, and may detect the target medical event using sophisticated detection algorithms requiring more memory space or computational resources. Examples of such algorithms may include machine learning algorithms, neural networks, decision trees, Bayesian networks, or clustering algorithms, among others. In an example, the event detector circuit 221 may use data sensed via multiple sensors to detect the target medical event. For example, in syncope detection, in addition to cardiac electrical activity sensors for detecting arrhythmias or cardiac pause, the event detector circuit 221 may use sensors to detect contextual information relevant to syncope, including one or more of sustained posture, postural change, physical activity level, sleep state, blood pressure, hydration level, respiratory rate, respiratory pattern, stress level, facial or vocal expressions, or emotional expressions, among others.

In an example, the event detector circuit 221 has a higher sensitivity than the AMD in detecting the target medical event. Higher sensitivity may be achieved by executing a more sensitive detection algorithm, or by tuning one or more parameters such as a detection threshold value. In some examples, the event detector circuit 221 may detect the medical event using patient medical history data. For example in arrhythmia or syncope detection, for patients having an arrhythmia or syncope history, the event detector circuit 221 may be configured to have a high sensitivity to arrhythmia or cardiac pause detection. However, for cryptogenic stroke patients, the event detector circuit 221 may be configured to have a high atrial fibrillation detection sensitivity without substantially altering the sensitivity to arrhythmia or pause detection. Examples of the event detector circuit 221 for detecting a syncope are discussed below, such as with reference to FIGS. 4A-B.

In addition to the detection information 222, the event detector circuit 221 may generate the detection confidence score 223 indicating a confidence about medical event detection. In an example, the confidence score may be determined using a signal quality measure of the physiological data acquired during the patient-triggered episodes, such as the signal to noise ratio (SNR) of the physiological data. A higher confidence score may be assigned to detections made using physiological data with higher signal quality, such as a higher SNR, than detections made using physiological data with poor signal quality. In another example where the detection is made based on a comparison of a signal metric generated from the physiological data to a detection threshold, the confidence score may be determined using a measure of deviation from the detection threshold. If a signal metric exceeds a detection threshold by a larger margin, then the resulting detection may assigned with a higher confidence score than are detections corresponding to signal metrics that exceed the detection threshold by a narrower margin. In another example, if the detection is made based on a comparison of the physiological data to a template signal representing the target medical event (e.g., as adjudicated by a clinician or an expert), the detection confidence score may be determined based on a degree of similarity between physiological data and the template signal. In yet another example, the detection confidence score may be determined using information about temporal relationship between the received episode (such as the patient-triggered episode) and the detected medical event. As previously discussed, the patient-triggered episode 212 may include timing of the patient reported symptom appearance, such as onset of symptom. The detection information 222 may include onset timing of the detected medical event. The temporal relationship between the patient-triggered episode and the event detection produced by the event detector circuit 221 may be measured by the timing difference between the symptom onset and the detection onset. A higher confidence score may be assigned to a detection if the detection onset is temporally within a specified range of the onset of the patient-triggered episode.

In some examples, the detection confidence score may be determined using information about patient medical history. For example, in detecting a cardiac arrhythmia or syncope, patient history of heart disease, previous syncopal or pre-syncopal episodes, patient demographic information, or historical patient-reported symptoms of arrhythmic or syncopal events may be used to determine the confidence score. A higher confidence score may be assigned to a detection if the patient demography or patient previously experienced medical events indicate that the patient is at a high risk of experiencing future arrhythmia or syncope events.

In some examples, the event detector circuit 221 may detect the medical event using physiological data sensed from multiple sensors, and the detection confidence score may be determined using information from multiple sensors, such as a measure of consistency among the sensor responses on the detection of the medical event. A higher confidence score may be assigned to a detection if more sensor responses are in an agreement on the presence or absence of the medical event, and a lower confidence score may be assigned if there is less consistency among the sensor responses. In some examples, the confidence score of a detection may evolve as the detection algorithm at event detector circuit 221 is tuned to improve detection performance (e.g., sensitivity and specificity) when applied medical events from multiple patients. For example, the detection algorithm may have parameter hysteresis for the missed detections that fall just below the set detection threshold. A higher confidence score may be assigned to the medical event that is detected using an algorithm having an improved detection performance.

The alignment detector circuit 224 may be configured to determine an alignment indicator indicating a degree of concordance between the detection of the target medical event and the received episode, such as the patient-triggered episode 212. In an example, the concordance may include a measure of agreement between the detection of the target medical event and the received episode, such as an agreement or disagreement on the presence or severity of an arrhythmia, a syncopal event, a WHF event, or other specified medical event. In another example, the concordance may include a measure of temporal alignment between an onset of the detected target medical event and an onset of the received episode, such as an onset of signs or symptoms the patient experiences. Examples of the alignment detector circuit 224 for determining an alignment indicator between a patient-triggered episode of syncope a machine-detected syncope (such as via the event detector circuit 221) are discussed below, such as with reference to FIGS. 4A-B.

The event prioritizer circuit 230 may be coupled to the event detector circuit 221 and the alignment detector circuit 224, and assign priority information to the received episode, such as the patient-triggered episode 212, using the generated alignment indicator and the detection confidence score. The event prioritizer circuit 230 may rank a plurality of episodes, such as patient-triggered episodes from the AMD, in a specified order of the priority. The ranked episodes may be presented to a clinician for episode review or adjudication. The priority information may be represented by a numerical value, such as in a scale from one to ten, where a higher value indicates a higher priority. The priority information may alternatively be represented by a categorical descriptor, such as "high", "medium", or "low" priority, among other priority categories.

Table 1 illustrates an example of priority information assigned to patient-triggered episodes according to the alignment indicator and the confidence indicator of the detection. In this example, a high priority is assigned to the patient-triggered episode if the alignment indicator indicates a concordance between the patient-triggered episode and the detection (alignment indicator="Yes"), and the confidence score exceeds a score threshold such that the detection confidence is "High". A low priority is assigned to the patient-triggered episode if the alignment indicator indicates a discordance between the patient-triggered episode and the detected medical event (alignment indicator="No"), and the confidence score of the detection exceeds a score threshold such that the detection confidence is "High". A medium priority is assigned to the patient-triggered episode if the confidence score falls below the score threshold such that the detection confidence is "Low", regardless of the degree of the alignment between the patient-triggered episode and the detection.

TABLE 1

| Alignment Indicator | Detection Confidence Score | Priority |
| --- | --- | --- |
| Yes | High | High |
| No | High | Low |
| Yes | Low | Medium |
| No | Low | Medium |

In some examples, the event prioritizer circuit 230 may assign the priority information further using a similarity metric between the received episode and one or more patient historical episodes stored in a patient database. The event prioritizer circuit 230 may include a comparator circuit that compares the similarity metric to one or more threshold values, or ranges of values, and categorize the received episode into one of a plurality of priority categories. In an example, the priority may be inversely related to the similarity metric, such that a lower priority may be assigned to a received episode that is more similar to the historical episodes, and a higher priority may be assigned to a received episode that is less similar to the historical episodes. The present inventors have recognized that a received episode that is dissimilar to the historical episodes may represent a medical condition not seen in patient medical history, or a substantial variation or progression of a historical medical event that may require immediate medical attention. Assigning a higher priority to such episodes with unprecedented characteristics may alert the healthcare provider to timely review the detected event, evaluate the patient status, or provide prompt medical intervention.

In some examples, the information about the historical episodes may include indicators of severity or clinical significance of the medical events associated with the historical episodes. The severity indicators may be provided by a clinician. In an example, historical medical events that result in physician intervention or hospitalization may be designated as severe historical episodes. In another example, severity may also be assigned by characteristics measured from the data in the medical event. For example, arrhythmias of longer duration, very high-rate tachycardias or low-rate bradycardias, or events with low blood pressure for an extended duration may be designated as severe episodes. The event prioritizer circuit 230 may compare the received episode (e.g., the patient-triggered episodes 212) to the severe historical episodes and to other non-severe historical episodes (such as annotated by a clinician, or those episodes not resulting in hospitalization or intervention). The event prioritizer circuit 230 may assign a higher priority to a received episode that is similar to the severe historical episode, or dissimilar to the severe or non-severe historical episodes, and assign a lower priority to a received episode that is similar to the non-severe historical episodes. The medical events with characteristics similar to severe medical events in patient medical history are likely of clinical significance. Assigning a higher priority to such events may ensure immediate medical attention and intervention as needed. In some examples, the event prioritizer circuit 230 may assign a high priority to an episode that is similar to the severe historical episode, a medium priority to an episode that is dissimilar to the severe or non-severe historical episodes, and a lowest priority to an episode that is similar to the non-severe historical episodes.

In some examples, the event analyzer circuit 220 may be configured to consolidate two or more received episodes into a cluster, and determine a representative episode for the cluster, such as a cluster center. Episodes within the same cluster may have similar signal characteristics, such that a distance between the signal feature vectors associated with any two patient-triggered events within an alert cluster falls below a threshold value. Clustering of patient-triggered episodes may provide benefits in patient management. The event prioritizer circuit 230 may assign the priority information to the representative episode. The representative episode may be presented to a clinician for review or adjudication, according to the assigned priority information. Because the episodes within the same cluster have similar signal characteristics, results from clinician review and adjudication of the representative episode may be applicable to the episodes within that cluster. As such, review and adjudication of all episodes within the cluster may be avoided, additional time and clinical resources may be saved, and the cost for patient management maybe reduced.

Clustering of the patient-triggered episodes may be performed using unsupervised learning algorithms. In an example, a K-means clustering may be used to minimize an objective function such as total squared distance between the physiological data associated with individual episodes and the cluster center. The cluster center for each cluster represents a centroid of the episodes within the cluster. In another example, a fuzzy C-means clustering may be used to minimize an objective function such as total weighted squared distance between the physiological data associated with individual episodes and the cluster center, where the weight represents a degree of membership of a particular episode being within the cluster. Other examples of the clustering may include hierarchical clustering that uses iterative update of clusters by merging the episodes using the similarity metrics, or mixture of Gaussians or other model-based clustering algorithms, among others. The patient-triggered episodes may alternatively be clustered using a supervised learning algorithm, such as clustering according to user-specified criteria or cluster characteristics. In an example, clusters may be formed according to one, or a subset of, the signal characteristics, such as one or more value ranges of a physiological parameter extracted from the patient-triggered episodes.

The user interface 240 may include an input unit and an output unit. In an example, at least a portion of the user interface 240 may be implemented in the external system 125. The input unit may receive user input for programming the event analyzer circuit 220 and the event prioritizer circuit 230, such as parameters and threshold values for detecting a target medical event, determining confidence score, determining the alignment indicator, or for prioritizing the received episodes. The input unit may include an input device such as a keyboard, on-screen keyboard, mouse, trackball, touchpad, touch-screen, or other pointing or navigating devices. In some examples, via the input unit and the output unit, a system user may interactively annotate or mark on the presentation of the detected medical event, such as by adjudicating the received episode. The output unit may rank a plurality of patient-triggered episodes in a specified order of priority, and present one or more of the ranked plurality of patient-triggered episodes to a user or a process. In an example, the patient-triggered episodes may be presented to a clinician in a descending order of the priority.

The output unit may include a display for displaying the patient physiological data associated with the detected medical event, intermediate measurements or computations such as signal characteristics, similarity metrics, episode priority information, among others. The output unit may generate a recommendation for adjusting AMD programming using the generated alignment indicator and the confidence score. Referring to Table 1, if a patient-triggered episode is assigned a high priority (corresponding to alignment indicator="Yes" and confidence score="High"), then the output unit may generate a recommendation for adjusting the detection parameters in AMD, such as to better capture future episodes that likely to align with patient reported symptoms. If a patient-triggered episode is assigned a low priority (corresponding to alignment indicator="No" and confidence score="High"), then the output unit may generate a recommendation for further patient training on reporting symptomatic episodes. If a patient-triggered episode is assigned a medium priority (corresponding to confidence score="Low"), then the output unit may generate a recommendation for tuning event detector circuit 221 using the patient-triggered episodes to improve the confidence of the detection. In an example, the recommendation may include using data sensed from additional sensors to detect the target medical event. The output unit may include a printer for printing hard copies of the detection information. The information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the system user about the detected medical events.

The optional therapy circuit 250 may be configured to deliver a therapy to the patient in response to the patient-triggered episode satisfying a specified condition, such as being assigned a high priority. As shown in Table 1, patient-triggered episode with a high priority is aligned with a high-confidence detection made by the event detector circuit 221. The patient-triggered episode thus more likely indicate presence of a true medical event that may require intervention. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 250 may modify an existing therapy, such as adjust a stimulation parameter or drug dosage.

Figure 3:
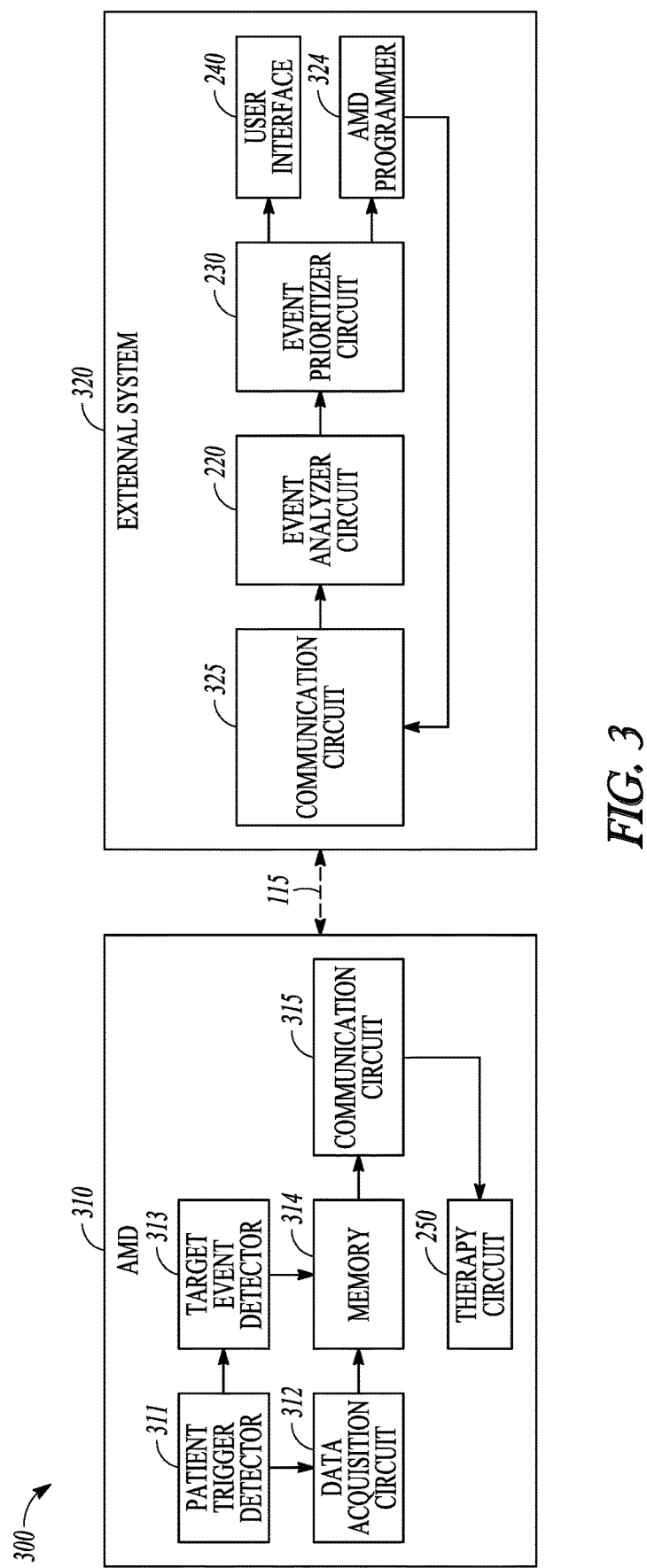
FIG. 3 illustrates generally another example of a medical event management system configured to evaluate and prioritize medical events detected from one or more patients.

FIG. 3 illustrates generally another example of a medical event management system 300 configured to evaluate and prioritize patient alerts of medical events detected from one or more patients. The alert management system 300 comprises an AMD 310 and an external system 320, communicatively coupled to each other via the communication link 115.

The AMD 310, which is an embodiment of the AMD 110 illustrated in FIG. 1, may include a target event detector 313 configured to detect a target medical event such as a cardiac arrhythmia, a cardiogenic syncope, an orthostatic or neurally-mediated syncope, or a WHF event, among others. Additionally or alternatively, the target event detector 313 may register a patient-triggered episode. The AMD 310 may include a patient trigger detector 311 that may be in wired or wireless communication with a triggering device. In an example, the triggering device may be incorporated within the AMD 310. In another example, the triggering device may be a wearable, hand-held, or otherwise ambulatory device coupled to the AMD 310. The triggering device may include a push button, a screen touch, or other actuator means that allows a user to generate activate a patient-triggered episode in the AMD 310. When the patient demonstrates certain signs or symptoms or experiences a precursor event indicative of a target medical event, a trigger may be produced and detected by the patient trigger detector 311. In some examples, the trigger may be activated by subjects other than the patient, such as a healthcare provider.

A detection of the patient trigger may activate the data acquisition circuit 312 to register the patient-triggered episode, and acquire physiological data such as one or more physiological signals. The physiological signals may be sensed from a patient via one or more implantable, wearable, or otherwise ambulatory sensors or electrodes associated with the patient. The sensors may be incorporated into, or otherwise associated with an ambulatory device such as the AMD 110. Examples of the physiological signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The data acquisition circuit 312 may include one or more sub-circuits to digitize, filter, or perform other signal conditioning operations on the received physiological signal.

The target event detector 313 may be coupled to the data receiver circuit 210 to detect a target medical event from the sensed physiological signals. In some examples, the physiological signals sensed from a patient may be stored in a storage device, such as an electronic medical record (EMR) system. The target event detector 313 may be configured to receive a physiological signal from the storage device in response to a user input or triggered by a specific event, and detect a target medical event from the received physiological signals.

The patient-triggered episodes and the associated physiological data, and the AMD detection of the target event, may be stored in the memory 314. The communication circuit 315 may transmit the physiological information to the external system 320 via the communication link 115. The physiological information may be transmitted continuously, periodically at scheduled time, or in response to a data interrogation command sent to the AMD 310 from the external system 320.

The external system 320, which is an embodiment of the external system 125, includes a communication circuit 325 that may receive the information including the patient-triggered episodes and the associated physiological data, and AMD detection of the target event. The external system 320 includes the event analyzer circuit 220 and the event prioritizer circuit 230. As discussed with reference to FIG. 2, the event analyzer circuit 220 may have a higher sensitivity than the target event detector 313 in the AMD 310 in detecting the target medical event. The event prioritizer circuit 230 may assign priority information to the patient-triggered episodes received from the AMD 310 using the alignment indicator between the patient-triggered episodes and the event detection at the event analyzer circuit 220, and the confidence score of the event detection. In an example, the event prioritizer circuit 230 may assign priority information to those patient-triggered episodes when the AMD 310 fails to detect the target medical event. Mismatch between the patient experienced symptoms and the AMD detection of medical events may have several causes, including a temporal discrepancy between the onset of symptoms and onset of physiological change detectable on a physiological signal, patient being overly sensitive to symptomatic changes and inclined to habitually trigger false positive episodes, thresholds for recording physiological data being set a level high above a patient symptomatic triggering threshold. In syncope detection, the patient-triggered episode of syncope may be of non-cardiac in nature or have no defined cardiac substrate (e.g., orthostatic syncope, neurally mediated syncope, or other unexplained syncope), and thus may not be detected when the target event detector 313 is configured to base the detection on cardiac arrhythmias or cardiac pause.

The prioritized patient-triggered episodes may be output to a clinician for review or adjudication via the user interface 240, as discussed previously with reference FIG. 2. The external system 320 may include an AMD programmer 324 that may generate commands for programming the AMD 310. The commands may include recommended adjustment of one or more event detection parameters for the target event detector 313, or data collection parameters for the data acquisition circuit 312, among others. The recommended adjustment may be confirmed or otherwise modified by a system user (such as a clinician) via the user interface 240, and forwarded to the AMD 310 via the communication link 115. In an example, the detection parameters used by the event analyzer circuit 220 may be transmitted to the AMD 310 for detecting target medical event.

FIGS. 4A-B illustrates generally graphs of patient-triggered episodes, and assignment of priority to these episodes. The medical events of interest in these examples are cardiac pauses, characterized by an absence of cardiac electrical activity for an extended period. The presence cardiac pause may be predictive of an onset of syncope. The AMD 310 may register the patient-triggered episodes upon detection of a patient trigger via the patient trigger detector 311. The patient trigger may be activated by a patient when experiencing a symptomatic syncope such as bradycardia or cardiac pause. The AMD 310 may additionally be configured to detect a pause indicative of syncope automatically via the target event detector 313.

FIG. 4A shows a patient-triggered episode 410 in response to a patient trigger at time T, when the patient experiences syncope. The episode may include a cardiac activity signal, such as an ECG or an intracardiac EGM. The data acquisition circuit 312 may continuously acquire the data in a rolling buffer, and write the acquired data to the memory 314 in response to the patient trigger. By way of example and not limitation, a time window for the episode data may begin ten minutes before the trigger point T, and ends five minutes after the trigger point T. The duration of the recorded signal may be adjustable, and is sufficient long to capture the changes in cardiac activity before, during, and after the syncope.

A cardiac activity signal portion 412, taken from the recorded episode 410 around time T1 prior to the patient trigger, contains two pause segments 415 and 416 each having duration of approximately 3.5 seconds and 3.3 seconds, respectively. In this example, the target event detector 313 in the AMD 310 is programmed to detect cardiac pause using a pause duration threshold of four seconds. Because both the pause segments 415 and 416 are shorter than the pause duration threshold, neither of the pause segments is detected by the AMD 310.

The registered patient-triggered episode may be transmitted to the external system 320, where the event detector circuit 221 in the external system detects the cardiac pause using a more sensitive algorithm than the target event detector 313 in the AMD 310. In this example, the event detector circuit 221 detects the cardiac pause by comparing it to a smaller pause duration threshold of two seconds. Because both of the pause segments 415 and 416 are longer than two seconds, the event detection circuit 221 may generate the detection information 222 indicating presence of pauses. The event detection circuit 221 may also perform one or more of a signal quality analysis of the patient-triggered episode, or temporal relationship between the patient-triggered episode and the detection performed by the event detector circuit 221, to determine a confidence score of the detection. As neither noise nor far-field cardiac electrical activity is detected in the pause segments 415 and 416, and the detection is temporally close to the time of trigger T, a high confidence score is determined for the detection. A detected pause is deemed to be temporally close to the time of trigger T if the detected pause falls within a detection window around the trigger T. In an example, the detection window begins at about 5-10 minutes before the trigger T, and ends at about 1-2 minutes after the trigger T.

Because both the patient trigger at the AMD 310 and the detection performed by the external system 320 indicate presence of a cardiac pause, the alignment detector circuit 224 generates an alignment indicator indicating such a concordance of detection. The event prioritizer circuit 230 may thus determine a high priority based on the alignment indicator and the high confidence of the detection, such as according to Table 1. The external system 320 may generate a recommendation for adjusting the detection parameters in AMD, such as to better capture future episodes that likely to align with patient reported symptoms.

FIG. 4B shows a patient-triggered episode 420 in response to a patient trigger at time T, when the patient feels lightheaded. Similar to 410, the episode includes a cardiac activity signal recorded during a time window that begins ten minutes before the trigger point T, and ends five minutes after the trigger point T. A cardiac activity signal portion 422, taken from the recorded episode 420 around time T2, contains consecutive pause segments 423, 424, and 425, each having a duration of approximately 2.6 seconds. None of these pauses is detected by the target event detector 313, which is programmed to detect a pause using a pause duration threshold of four seconds.

The registered patient-triggered episode is transmitted to the external system 320, where the event detector circuit 221 detects the pause segments 423, 424, and 425 using a pause threshold of two seconds. The event detection circuit 221 additionally detects far-field (FF) electrical activities in each of the pause segments 423, 424, and 425, such as the FF electrical activities 426, 427, and 428 during the pause segment 423. The event detection circuit 221 also detects repeated pause pattern. Both the presence of FF electrical activity during the detected pause segments and the repeated pause pattern reduce the confidence that the syncope is cardiac in nature. As such, the event detection circuit 221 determines a low confidence score for the syncope detection. The event prioritizer circuit 230 may thus determine a medium priority, according to Table 1. The external system 320 may generate a recommendation for tuning event detector circuit 221 using the patient-triggered episodes, or use additional sensors to detect syncope. In some examples, the event prioritizer circuit 230 may identify and flag a patient-triggered episode as an "advanced" episode reserved for a more experienced clinician to review, such as to determine its clinical etiology. For example, the episode 420 may be flagged as an advanced episode because of the uncertainty of the etiology that gives rise to the morphology of the signal portion 422. The electrical activities 426, 427, 428 may be signatures of atrial activities (e.g., far-field P waves), and the episode 420 represents an atrioventricular (A-V) block, which is a physiological substrate for syncope. Alternatively, the electrical activities 426, 427, 428 may be signatures of ventricular activities (e.g., QRS complexes), which is not evidence of a physiological substrate for syncope. By episode flagging, time and effort of a more experienced clinician can be reserved for the advanced episodes, and overall cost saving may be achieved.

Figure 5:
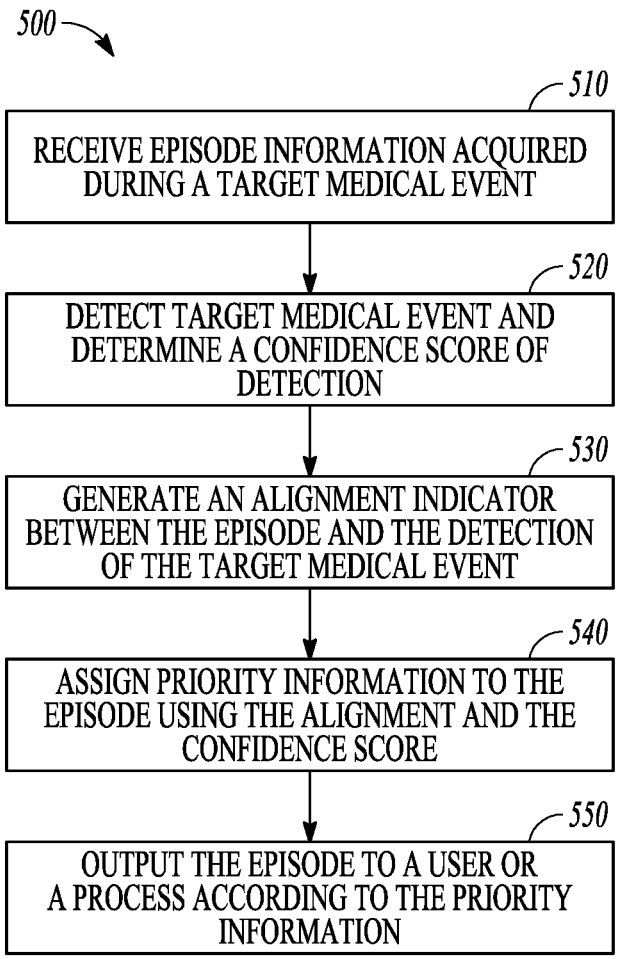
FIG. 5 illustrates generally an example of a method for prioritizing medical events detected by an ambulatory medical device (AMD).

FIG. 5 illustrates generally an example of a method 500 for prioritizing medical events detected by an ambulatory medical device (AMD). The method 500 may be implemented and executed in an ambulatory medical device such as an implantable or wearable medical device, or in a remote patient management system. In an example, the method 500 may be implemented in and executed by one or more devices in the external system 125 or the external system 320.

The method 500 begins at 510, where physiological information acquired during a medical event may be received. The episode may include an event automatically detected by the AMD, such as a cardiac arrhythmia, a syncopal event, or a worsening heart failure (WHF) event, among others. Additionally or alternatively, the episode may include a patient-triggered episode registered by the AMD. As previously discussed with reference to FIG. 3, the trigger may be activated by the patient or other healthcare professional via a triggering device that is incorporated in the AMD, or a wearable, hand-held, or otherwise ambulatory device coupled to the AMD. A trigger may be produced when the patient demonstrates certain signs or symptoms or experiences a precursor event indicative of a target medical event such as a cardiac arrhythmia, a syncopal event, or a WHF event. In response to the patient trigger, the patient-triggered episode may be registered, and the physiological data (such as one or more physiological signals sensed by physiological sensors) may be acquired such as via the data acquisition circuit 312. Examples of the physiological signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. In addition to the physiological signals in response to the patient trigger, the information about the patient-triggered episode may include patient input about presence of the target medical event, severity of the symptoms, timing of the symptoms such as onset time, termination time, or variation of symptoms during the patient-triggered episode, among others.

At 520, a target medical event may be detected using the received episodes, such as the physiological data acquired during the patient-triggered episodes. In an example, such event detection may be performed in an external system, such as the external system 325. The detection may be performed offline, such that the detection decision may not be provided in real time as the signal data are acquired and fed into a detector. Compared to real-time or near real-time detection of the target medical event, the offline detection may have a higher sensitivity than the detection algorithm used by the AMD for detecting the target medical event. For example, the detection algorithm used at 520 may involve a comparison of a signal metric to a detection threshold having a lower threshold value than the threshold used by the AMD for real-time detection of the target medical event. Additional sensor data may also be used at 520 to detect the target medical event.

A detection confidence score indicating a confidence about medical event detection may also be generated at 520. In an example, detections made using physiological data with higher signal quality, such as a higher signal-to-noise ratio (SNR), may be assigned a higher confidence score than detections made using physiological data with poor signal quality. In another example, detections that correspond to a signal metric that exceeds the detection threshold by a larger margin may be assigned a higher confidence score than detections made out of a signal metric exceeding the detection threshold by a narrower margin. In another example, the detection confidence score may be determined based on a degree of similarity between the signal features of the physiological data and the signal features of a template signal. In yet another example, the detection confidence score may be determined using information about temporal relationship between the received episode (e.g., a patient-triggered episode) and the detected medical event obtained at 520, such as timing difference between an onset of patient-triggered episode and the detected onset of the medical event. A higher confidence score may be assigned to a detection if the onset of detection is temporally within a specified range of the onset of the patient-triggered episode. The detection confidence score may be determined further using information about patient medical history. For example, patient previous syncopal or presyncopal episodes, demographic information, historical patient-reported symptoms of arrhythmic or syncopal events, among other risk factors may be used to determine the confidence score. In some examples, the detection confidence score may be determined based on a measure of consistency among multiple sensor responses on the detection of the medical event.

At 530, an alignment indicator between the episode received at 510 and the detection of the target medical event at 520 may be determined, such as by using the alignment detector circuit 224. The alignment indicator indicates a degree of concordance between the detection of the target medical event and the received episode. The concordance may include agreement or disagreement on the presence or severity of an arrhythmia, a syncopal event, a WHF event, or other specified medical event. Additionally or alternatively, the concordance may include a measure of temporal alignment between the onset of the detected target medical event and the onset of the received episode, such as an onset of patient symptoms.

At 540, priority information may be assigned to the received episode such as by using the event prioritizer circuit 230. The priority information may be generated using the alignment indicator and the detection confidence score. The priority information may be represented by a numerical value or a categorical descriptor. An example of priority assignment is provided in Table 1. The priority information may be used to rank a plurality of episodes, such as patient-triggered episodes as detected by an AMD, in a specified order of the priority and presented to a clinician for episode review or adjudication. In some examples, the priority information may be determined further using a similarity metric between the received episode and one or more patient historical episodes stored in a patient database. For example, a higher priority may be assigned to a received episode that is less similar to the historical episodes. In some examples, the information about the historical episodes may include indicators of severity or clinical significance of the medical events associated with the historical episodes. A received episode, such as a patient-triggered episode, may be compared to one or more of severe historical episodes such as the episodes leading to hospitalization or intervention, or non-severe historical episodes such as those adjudicated by a clinician. The episode may be assigned a higher priority if it is similar to the severe historical episode, or if it is dissimilar to the severe or non-severe historical episodes. The episode may be assigned a lower priority if it is similar to the non-severe historical episodes.

At 550, the episode may be output to a user (e.g., a clinician) or a process according to the assigned priority information. In an example, the patient physiological data associated with the detected medical event, intermediate measurements or computations may also be output to the clinician such as on a display, where a system user may interactively annotate or mark on the presentation of the detected medical event, or adjudicate the detection. Additionally or alternatively, a hard copy of the detection information may be generated.

In some examples, at 550, a recommendation may be generated and provided to the user. The recommendation may include one or more of further diagnostic tests to be performed or therapies to administer. The recommendation may also include recommendations for adjusting AMD programming using the generated alignment indicator and the confidence score.

The method 500 may include an optional step of delivering a therapy to the patient in response to the detection of the medical event, such as via the optional therapy circuit 250 as illustrated in FIG. 2. The therapy may be delivered in response to the patient-triggered episode satisfying a specified condition, such as being assigned a high priority. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy may be modified such as by adjusting a stimulation parameter or drug dosage.

Figure 6:
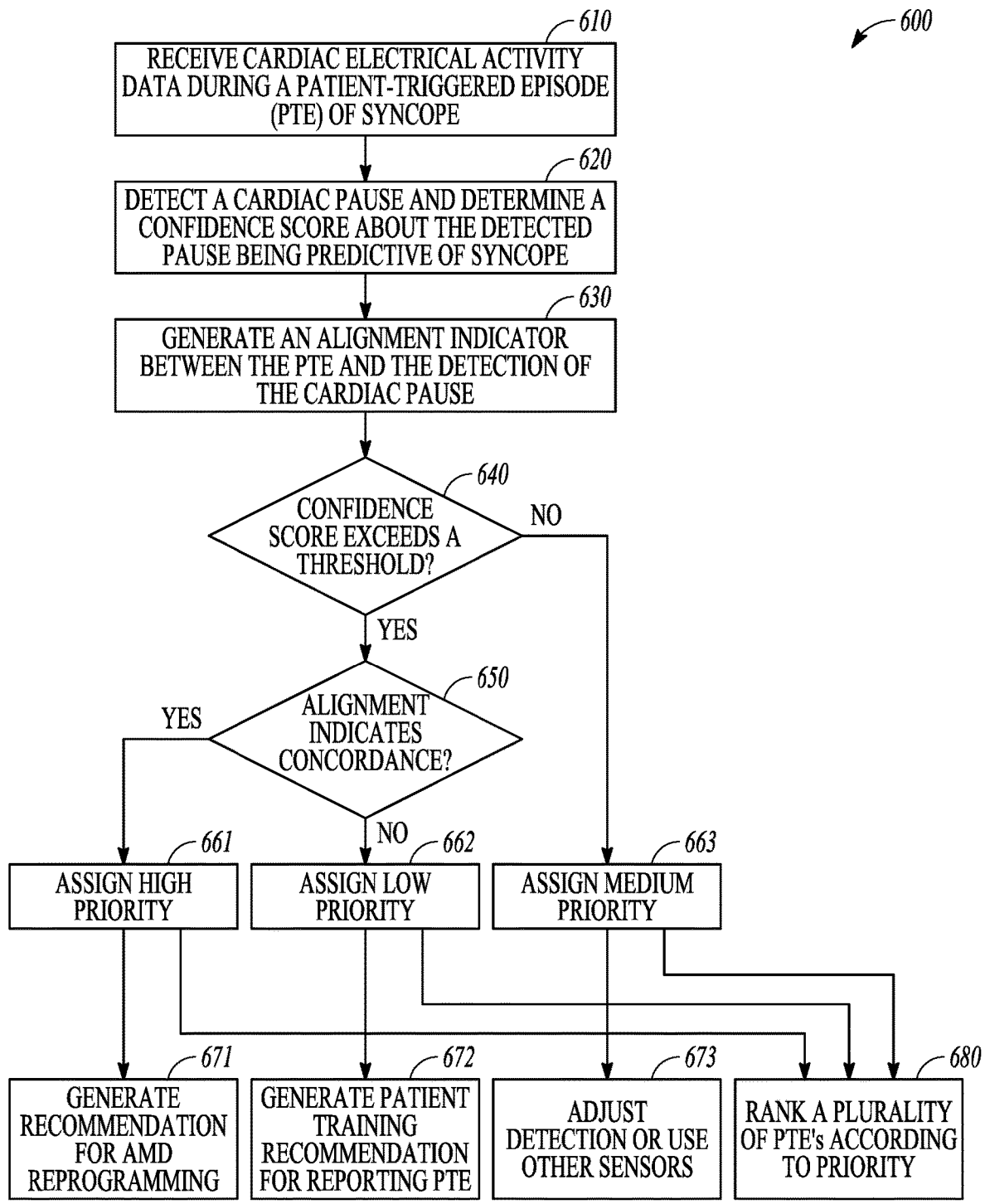
FIG. 6 illustrates generally an example of a method for prioritizing patient-triggered episodes of syncope using a comparison of the episode and a device-generated syncope detection.

FIG. 6 illustrates generally an example of a method 600 for prioritizing patient-triggered episodes of syncope using a comparison of the episode and a device-generated syncope detection. The method 600 may be an embodiment of the method 500. In an example, the method 600 may be implemented in and executed by the medical event management system 200 or the medical event management system 300. In an example, the method may be implemented in the external system external system 320, and configured to evaluate and prioritize the patient-triggered episodes registered in the AMD 310.

The method 600 begins at 610 by receiving cardiac electrical activity data during a patient-triggered episode (PTE) of syncope. The cardiac activity data may include ECG or an intracardiac EGM recorded in an AMD during a specified time window in response to a patient trigger when the patient experiences one or more signs or symptoms of syncope or presyncope, such as lightheadedness, sweating, blurred vision, confusion, feeling warm, nausea or vomiting, among others. The cardiac activity data may be acquired and stored in an AMD, and transmitted to an external system for evaluation and prioritization. The duration of the recorded cardiac activity signal may begin at a specified time before the patient trigger and ends at a specified time after the patient trigger to capture the changes in cardiac activity before, during, and after the syncope.

At 620, a medical event, such as a cardiac pause or an arrhythmia, may be detected, such as using the target event detector 313. Cardiac pause or cardiac arrhythmia may be precursors of presyncope or syncope. Cardiac pause may be detected if no cardiac event is detected for a sustained period of time exceeding a specified pause duration threshold. In the examples as illustrated in FIGS. 4A-B, the pause duration threshold may be approximately two seconds. In addition to pause detection, a confidence score about the detected pause being predictive of syncope may also be determined at 620. As previously discussed at step 520 of the method 500, confidence score of the detection may be determined using a variety of methods. In an example, a quality of the cardiac activity signal associated with the patient-triggered episode may be analyzed. If the signal has a high signal-to-noise ratio (SNR), or if no far-field cardiac electrical activity is detected in the pause segments, then a high confidence score is assigned. Confidence score may also be determined using a temporal relationship between the patient-triggered episode and the pause detection at 620. A high confidence score may be assigned if the onset of pause detection is temporally close to the patient trigger.

At 630, an alignment indicator between the PTE and the detected medical event, such as the detected cardiac pause, may be generated, such as using the alignment detector circuit 224. For example, if the patient trigger and the detection at 620 both indicate presence of a cardiac pause, then an alignment indicator of concordance of detection may be generated.

At 640, the confidence score generated at 620 may be compared to a score threshold. If the confidence score exceeds the score threshold, the alignment indicator generated at 630 may be evaluated at 650. If the alignment indicator indicates a concordance on the decision of presence of cardiac pause or other precursor of syncope or presyncope, then a high priority may be assigned to the PTE at 661. If at 650 the syncope detection at 620 does not concord with the patient trigger (e.g., patient-triggered episode indicates occurrence of syncope symptom, but not syncope is detected at 620), then a low priority may be assigned to the PTE at 662. If at 640 the confidence score falls below the score threshold, then a medium priority may be assigned to the PTE at 663.

Recommendations may be generated and presented to a user such as a clinician. For a patient-triggered episode assigned with a high priority at 661, a recommendation for adjusting the detection parameters in AMD may be generated at 671, such as to better capture future episodes that likely to align with patient reported symptoms. For a patient-triggered episode assigned with a low priority at 662, a recommendation for further patient training on reporting symptomatic episodes may be generated at 672. For a patient-triggered episode assigned with a medium priority at 663, a recommendation for tuning event detection at 520 using the patient-triggered episodes may be generated at 673 to improve the confidence of the detection. At 680, the assigned priority information may be used to rank a plurality of PETs in a specified order, such as a descending order. The ranked episodes may be presented to a user or a process.

Figure 7:
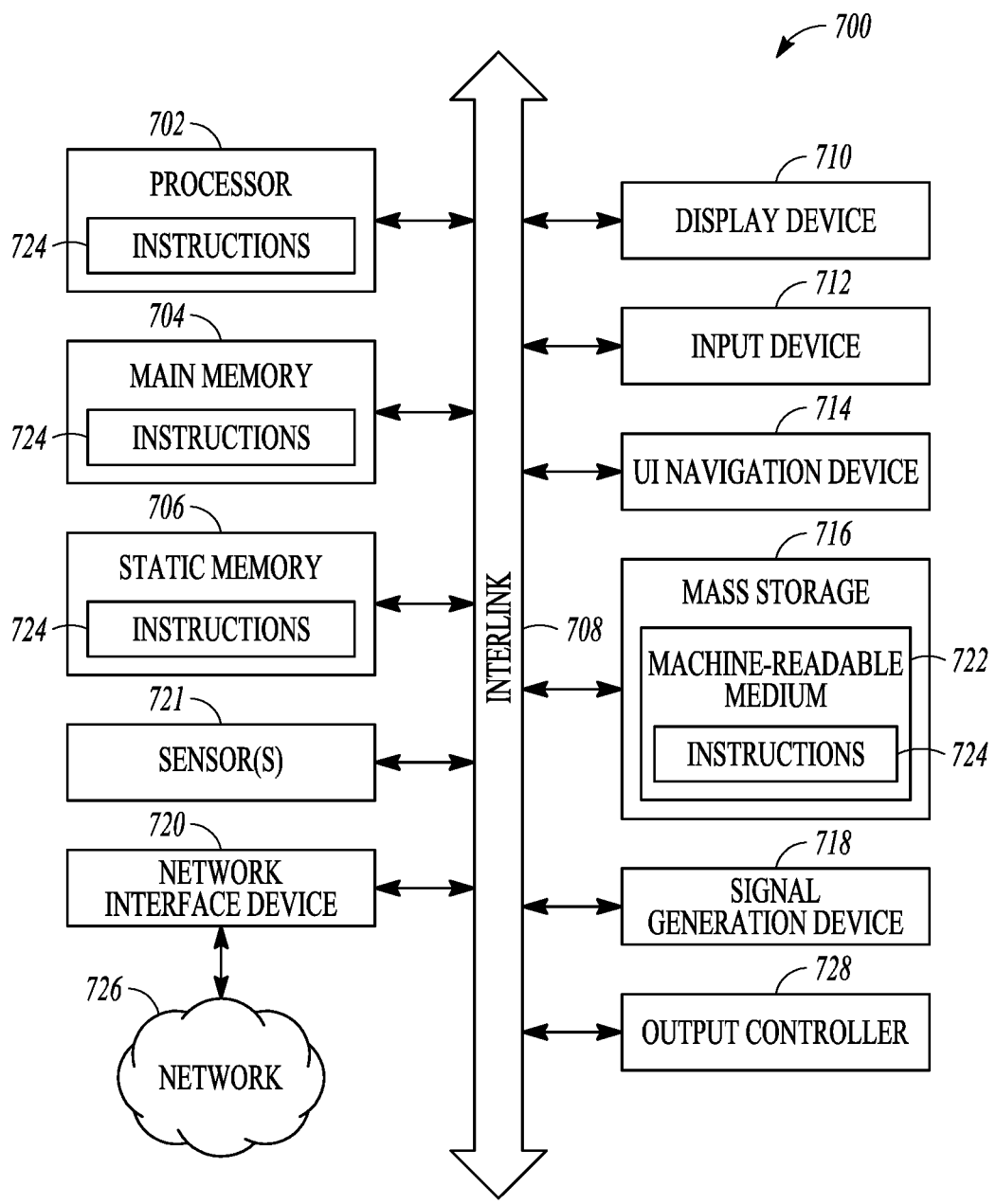
FIG. 7 illustrates generally a block diagram of an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the LCP device, the IMD, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc. connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communication network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communication network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for prioritizing medical events detected by an ambulatory medical device (AMD), the system comprising:
   a receiver circuit configured to receive physiological information from the AMD corresponding to a patient-triggered episode;
   an event analyzer circuit configured to analyze the received physiological information corresponding to the patient-triggered episode, and to determine a confidence score for the patient-triggered episode;
an event prioritizer circuit configured to assign priority information to the received patient-triggered episode using the confidence score, wherein the patient-triggered episode includes information about patient-reported sign or symptom, and the event analyzer circuit is configured to detect a medical event and generate an alignment indicator indicating a concordance between the information about patient-reported sign or symptom and the detected medical event; and
an output unit configured to display, or provide an alert of, the detected medical event.

2. The system of claim 1, wherein the event analyzer circuit is configured to perform offline analysis of the received physiological information corresponding to the patient-triggered episode.

3. The system of claim 1, wherein the event analyzer circuit is configured to determine the confidence score using a signal to noise ratio (SNR) of physiological data from the received physiological information.

4. The system of claim 1, wherein the event analyzer circuit is configured to determine the confidence score using information about temporal relationship between the information about patient-reported sign or symptom and the detected medical event.

5. The system of claim 1, wherein the event prioritizer circuit is configured to assign the priority information to the patient-triggered episode including one or more of:
a high priority if the confidence score exceeds a score threshold and the alignment indicator indicates a concordance between the patient-triggered episode and the detected medical event;
a low priority if the confidence score exceeds a score threshold and the alignment indicator indicates a discordance between the patient-triggered episode and the detected medical event; or
a medium priority if the confidence score falls below the score threshold.

6. The system of claim 1, comprising an external device operatively in communication with the AMD, the external device including one or more of the receiver circuit, the event analyzer circuit, or the event prioritizer circuit.

7. The system of claim 6, wherein the external device is configured to:
receive from the AMD the physiological information corresponding to the patient-triggered episode when the AMD fails to detect a medical event; and
detect the medical event via the event analyzer circuit with a higher sensitivity than the AMD in detecting the medical event.

8. The system of claim 1, wherein the physiological information includes cardiac electrical activity data corresponding to a patient-triggered syncopal episode, and wherein the event analyzer circuit is configured to:
detect a cardiac arrhythmia using the cardiac electrical activity data;
determine a confidence score about the detected cardiac arrhythmia being predictive of syncope; and
generate an alignment indicator indicating a degree of concordance between the patient-triggered episode and the detected cardiac arrhythmia.

9. The system of claim 8, wherein the cardiac arrhythmia includes a cardiac pause, and the event analyzer circuit is configured to determine the confidence score about the detected pause being predictive of syncope using one or more of:
a signal to noise ratio (SNR) of the cardiac electrical activity data; or
a detection of far field cardiac electrical activity during the cardiac pause.

10. The system of claim 1, comprising an output circuit configured to rank a plurality of patient-triggered episodes in a specific order of the assigned priority information, and to present one or more of the ranked plurality of patient-triggered episodes to a user or a process.

11. The system of claim 10, wherein the output circuit is configured to generate a recommendation for adjusting AMD programming using the confidence score.

12. The system of claim 1, wherein the event prioritizer circuit is configured to assign priority information to the received patient-triggered episode further based on the alignment indicator.

13. A method for prioritizing medical events detected by an ambulatory medical device (AMD), the method comprising:
receiving, via a receiver circuit, physiological information corresponding to a patient-triggered episode, the patient-triggered episode including information about patient-reported sign or symptom;
analyzing the received physiological information corresponding to the patient-triggered episode via an event analyzer circuit to detect a medical event;
generating an alignment indicator indicating a concordance between the information about patient-reported sign or symptom and the detected medical event;
determining a confidence score for the patient-triggered episode;
assigning priority information to the received physiological information via an event prioritizer circuit using the confidence score; and
displaying or providing an alert of the detected medical event.

14. The method of claim 13, wherein determining the confidence score of medical event detection includes using one or more of:
a signal to noise ratio (SNR) of physiological data in the received physiological information; or
information about temporal alignment between the information about patient-reported sign or symptom and the detected medical event.

15. The method of claim 13, wherein assigning the priority information to the patient-triggered episode includes assigning one or more of:
a high priority if the confidence score exceeds a score threshold and the alignment indicator indicates a concordance between the patient-triggered episode and the detected medical event;
a low priority if the confidence score exceeds a score threshold and the alignment indicator indicates a discordance between the patient-triggered episode and the detected medical event; or
a medium priority if the confidence score falls below the score threshold.

16. The method of claim 13, wherein:
receiving the physiological information includes receiving the physiological information corresponding to the patient-triggered episode when the AMD fails to detect the medical event; and
detecting the medical event includes using the event analyzer circuit with a higher sensitivity than the AMD to detect the medical event.

17. The method of claim 13, wherein the physiological information includes cardiac electrical activity data corresponding to a patient-triggered syncopal episode, and the medical event includes a cardiac pause indicative of syncope, the method comprising:
- detecting the cardiac pause using the cardiac electrical activity data;
- determining a confidence score about the detected pause being predictive of syncope using one or more of a signal to noise ratio (SNR) of the cardiac electrical activity data or a detection of far field cardiac electrical activity during the cardiac pause; and
- generating an alignment indicator indicating a degree of concordance between the patient-triggered episode and the detected cardiac pause.

18. The method of claim 13, comprising ranking a plurality of patient-triggered episodes in a specified order of the assigned priority information, and outputting one or more of the ranked plurality of patient-triggered episodes to a user or a process.

19. The method of claim 13, wherein assigning priority information to the received physiological information is further based on the alignment indicator.

20. A system for prioritizing medical events detected by an ambulatory medical device (AMD), the system comprising:
- a receiver circuit configured to receive physiological data from the AMD and information about patient-reported sign or symptom;
- an event analyzer circuit configured to analyze the received physiological data to detect a medical event, and to generate an alignment indicator indicating a concordance between the information about patient-reported sign or symptom and the detected medical event;
- an event prioritizer circuit configured to assign priority information to the detected medical event using the alignment indicator; and
- an output unit configured to display, or provide an alert of, the detected medical event.

* * * * *